US006735472B2

(12) United States Patent
Helland

(10) Patent No.: US 6,735,472 B2
(45) Date of Patent: May 11, 2004

(54) METHOD OF DEFIBRILLATING A HEART WITH ELECTRODE CONFIGURATIONS INCLUDING A LEFT VENTRICULAR DEFIBRILLATION ELECTRODE

(75) Inventor: John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 85 days.

(21) Appl. No.: 09/771,268

(22) Filed: Jan. 26, 2001

(65) Prior Publication Data

US 2002/0103507 A1 Aug. 1, 2002

(51) Int. Cl.$^7$ .................................................. A61N 1/18
(52) U.S. Cl. ............................. 607/5; 607/15; 607/123
(58) Field of Search ........................... 607/4–5, 15, 7, 607/9, 115, 123, 148

(56) References Cited

U.S. PATENT DOCUMENTS

| 4,548,203 | A |   | 10/1985 | Tacker, Jr. et al. ...... 128/419 D |
|---|---|---|---|---|
| 4,708,145 | A | * | 11/1987 | Tacker et al. |
| 5,324,309 | A | * | 6/1994 | Kallok |
| 5,344,429 | A | * | 9/1994 | Smits |
| 5,466,254 | A |   | 11/1995 | Helland ...................... 607/123 |
| 5,531,764 | A | * | 7/1996 | Adams et al. |
| 5,720,768 | A | * | 2/1998 | Verboven-Nelissen |
| 5,814,079 | A |   | 9/1998 | Kieval ............................ 607/4 |
| 5,836,975 | A |   | 11/1998 | DeGroot ........................ 607/5 |
| 5,836,976 | A |   | 11/1998 | Min et al. ....................... 607/6 |
| 5,865,838 | A |   | 2/1999 | Obel et al. ..................... 607/5 |
| 5,902,324 | A |   | 5/1999 | Thompson et al. ............ 607/9 |
| 5,968,079 | A |   | 10/1999 | Warman et al. ................ 607/5 |
| 5,978,704 | A |   | 11/1999 | Ideker et al. ................... 607/5 |
| 5,987,354 | A |   | 11/1999 | Cooper et al. ................. 607/5 |
| 6,006,131 | A |   | 12/1999 | Cooper et al. ................. 607/5 |
| 6,096,064 | A | * | 8/2000 | Routh |
| 6,205,357 | B1 |   | 3/2001 | Ideker et al. ................. 607/14 |
| 6,370,427 | B1 | * | 4/2002 | Alt et al. |

\* cited by examiner

*Primary Examiner*—Mark Bockelman
*Assistant Examiner*—Jeanne Yu

(57) ABSTRACT

An implantable universal pacing and defibrillating system provides efficacious sensing, pacing, and cardioversion/defibrillation in all four chambers of the heart. The system includes three leads with one lead being configured for implant in the coronary sinus for sensing, pacing, and defibrillating in both the left atrium and left ventricle. The leads also provide a plurality of different electrode configurations for both ventricular and atrial defibrillation. Sequential primary and secondary defibrillation shocks may be employed to advantage for depolarizing essentially all of the ventricular or atrial myocardium.

9 Claims, 8 Drawing Sheets

METHOD OF DEFIBRILLATING A HEART WITH ELECTRODE CONFIGURATIONS INCLUDING A LEFT VENTRICULAR DEFIBRILLATION ELECTRODE

FIELD OF THE INVENTION

The present invention generally relates to a method of defibrillating a heart with an implantable cardiac stimulation system. The present invention more particularly relates to such a method wherein a defibrillating stimulation pulse is applied simultaneously across a plurality of different chambers of the heart.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the heart left side, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Cardiac leads intended for use in the left heart via the coronary sinus region are difficult to position due to the tortuous venous routes of the human anatomy. Moreover, to provide both pacing and defibrillation of both the left atrium and the left ventricle from the coronary sinus region with multiple leads employing the appropriate types of electrodes is extremely difficult given the space constrains to accommodate multiple leads in the coronary sinus region. Hence, such implants are too cumbersome, difficult, and time consuming to perform and would likely result in compromised performance or system malfunction.

Universal pacing and defibrillation systems, capable of pacing and defibrillating all four heart chambers of the heart would require numerous pacing and defibrillation electrodes to be employed within the heart and its coronary venous system. To implement such a universal pacing and defibrillation system utilizing current state of the art lead configuration approaches, an inordinate number of leads would be required. This would result in lengthy implant procedures and possibly more leads than the human anatomy is able to accommodate. An inordinate number of leads may also make it difficult to accurately locate each electrode at a most efficacious position within the heart.

Efforts to minimize the number of required leads could also be fraught with potential obstacles. Such an effort would most likely include loading a lead up with too many electrodes. While this would reduce the number of required leads, such a lead would be difficult to implant. More importantly, owing to the differences in physiology from one patient to another, such a lead would most likely not "fit" a large number of patients in terms of resulting efficacious electrode positioning.

Efforts to achieve a universal pacing and defibrillation system, if successful, could provide significant improved therapies. Coordinated right heart and left heart pacing therapies would be made possible. Further, improved defibrillation therapies would also be made possible. Such therapies could include improved defibrillation energy distribution within the heart and/or new and improved sequential defibrillation pulse techniques.

SUMMARY OF THE INVENTION

The present invention provides a method of providing defibrillation stimulation to a heart with an implantable cardiac stimulation system wherein the stimulation pulse is applied with electrode configurations to deliver the stimulation pulse simultaneously across a plurality of chambers of the heart.

In accordance with one aspect of the invention, the stimulation pulse is applied with a first electrode configuration between a first chamber of the heart and third and fourth chambers of the heart and simultaneously applied with a second electrode configuration between a second chamber of the heart and the third and fourth chambers of the heart, one of the chambers of the heart being the left ventricle. In accordance with this aspect of the present invention, the first chamber may be the right atrium, the second chamber may be the right ventricle, the third chamber may be the left atrium and the fourth chamber may be the left ventricle. Alternatively, the first chamber may be the right atrium, the second chamber may be the left atrium, the third chamber may be the right ventricle, and the fourth chamber may be the left ventricle.

In accordance with a further aspect of the present invention, the conductive case of the implantable device may be used as an electrode. For example, the stimulation pulse may be applied with a third electrode configuration between the case and either the first and second chambers or the third and fourth electrodes.

In accordance with another aspect of the present invention, the stimulation pulse may be applied between the left ventricle of the heart and the case while simultaneously applying the stimulation pulse between a further chamber other than the left ventricle and the case. The further chamber may be the right ventricle.

In accordance with further aspects of the present invention, a defibrillation electrode is placed in electrical contact with each of the four chambers of the heart, a first common connection is formed with a first plurality of the electrodes, a second common connection is formed with a second plurality of the electrodes, and the stimulation pulse is delivered between the first and second connections. The electrodes for the left atrium and left ventricle may be electrically contacted with the left atrium and left ventricle by placing the electrodes within the coronary sinus region of the heart adjacent those chambers.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
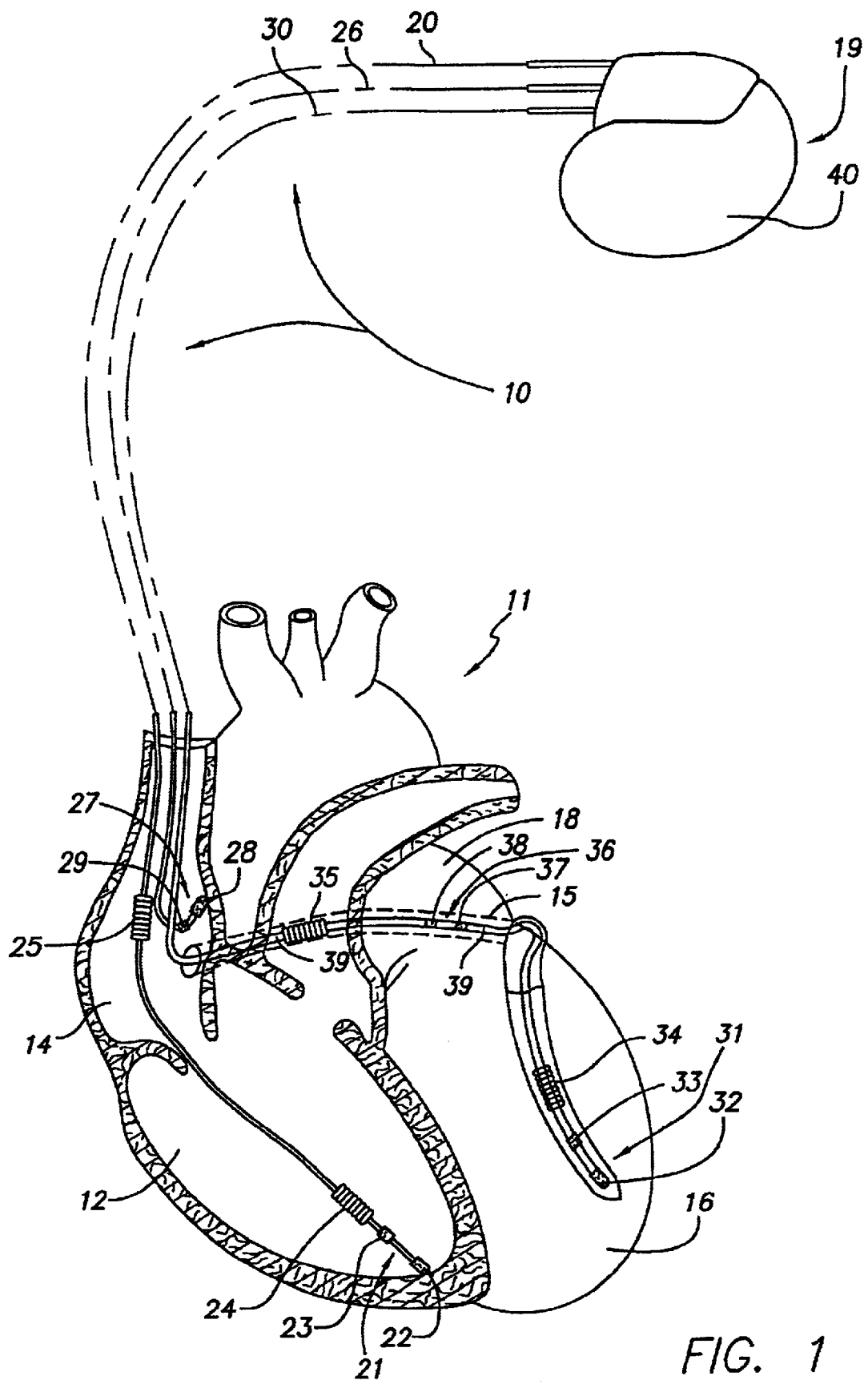
FIG. 1 illustrates a universal pacing and defibrillating system embodying the present invention including an implantable stimulation device in electrical communication with three leads implanted into a patient's heart for delivering multi-chamber pacing stimulation and defibrillation on therapy.

As shown in FIG. 1, there is a universal pacing and defibrillation system 10 embodying the present invention including a stimulation device 19 in electrical communication with a patient's heart 11 by way of three leads, 20, 26 and 30, suitable for delivering multi-chamber stimulation and shock therapy. To sense atrial cardiac signals and to provide right atrial chamber pacing stimulation therapy, the stimulation device 19 is coupled to an implantable right atrial lead 26 having an electrode pair 27 including a right atrial tip electrode 28 and a right atrial ring electrode 29. Typically, the electrodes 28 and 29 are implanted in the appendage of the patient's right atrium.

To sense left atrial and ventricular cardiac signals, to provide left atrial and ventricular pacing therapy, and to provide left atrial and ventricular defibrillation shocks, the stimulation device 19 is coupled to a "coronary sinus" lead 30 designed for placement in the "coronary sinus region" via the ostium of the coronary sinus 15 for positioning a defibrillation electrode and at least one pacing electrode adjacent to the left ventricle 16 and a defibrillation electrode and at least one pacing electrode adjacent to the left atrium 18. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, in accordance with one aspect of the present invention, the coronary sinus lead 30 is designed to receive left ventricular cardiac signals and to deliver left ventricular pacing therapy using an electrode pair 31 including a left ventricular tip electrode 32 and a left ventricular ring electrode 33. For shocking from or to the left ventricle 16, the lead 30 includes a left ventricular coil electrode 34. The coronary sinus lead 30 is further designed to receive left atrial cardiac signals and to deliver left atrial pacing therapy using an electrode pair 36 including electrodes 37 and 38. For shocking from or to the left atrium, the lead 30 further includes a left atrial coil electrode 35. The left atrial electrodes 35, 37 and 38 comprise an electrode assembly 39. In order to provide this functionality, the left ventricular coil electrode 34 and the electrode assembly 39 are spaced apart on the lead 30 so that when electrodes 32, 33 and 34 are adjacent to and in electrical contact with the left ventricle 16, the electrodes 35, 37 and 38 of electrode assembly 39 are within the coronary sinus 15 adjacent to and in electrical contact with the left atrium 18.

The stimulation device 19 is also shown in electrical communication with the patient's heart 11 by way of an implantable right ventricular lead 20 having, in this embodiment, a pacing and sensing electrode pair 21 including a right ventricular tip electrode 22 and a right ventricular ring electrode 23. The lead 20 further includes defibrillation electrodes including a right ventricular (RV) coil electrode 24, and an SVC/RA coil electrode 25. Typically, the right ventricular lead 20 is transvenously inserted into the heart 11 so as to place the right ventricular tip electrode 22 in the right ventricular apex so that the RV coil electrode 24 will be positioned in the right ventricle 12 and the RA coil electrode 25 will be positioned in the right atrium 14 or superior vena cava. As is well known in the art, the RA coil electrode 25 may be positioned in either the right atrium or superior vena cava. Hence, for purposes of brevity, the electrode 25 will be referred to herein as the RA coil electrode 25 and should be understood to also include placement of the electrode 25 in either the right atrium or superior vena cava with equal effect. Accordingly, the right ventricular lead 30 is capable of receiving cardiac signals, and delivering stimulation in the form of pacing and shock therapy to the right ventricle.

Figure 2:
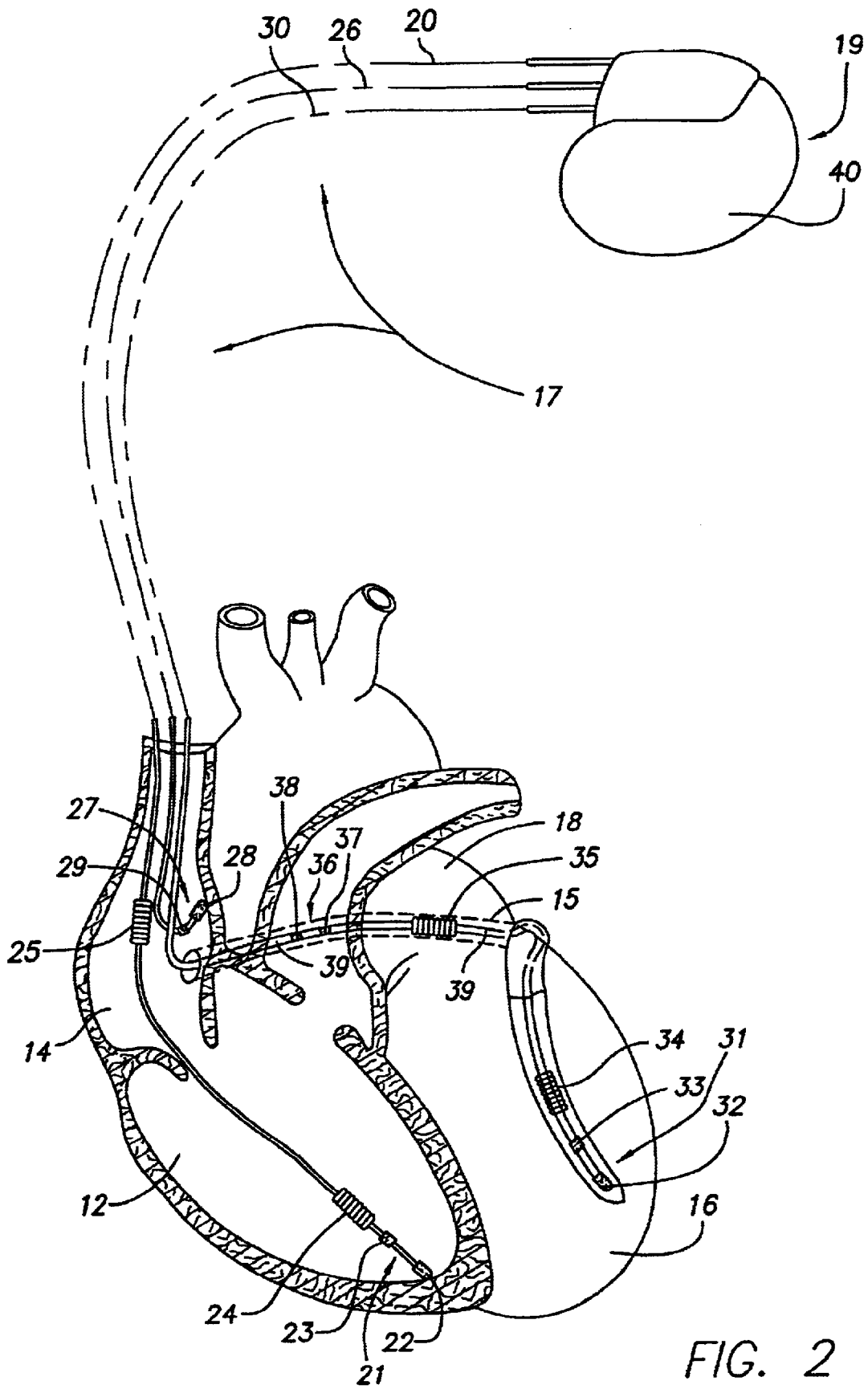
FIG. 2 illustrates another universal pacing and defibrillating system embodying the present invention including an implantable stimulation device in electrical communication with three leads implanted into a patient's heart for delivering multi-chamber pacing and defibrillation therapy.

FIG. 2 shows another universal pacing and defibrillation system 17 embodying the present invention. The system 17 is similar to the system 10 of FIG. 1 except for a few differences. Hence, only the differences will be described herein.

One difference relates to the RA coil electrode 25. Here, instead of being carried by the RV lead 20, it is carried by the RA lead 26. As with the system 10 of FIG. 1, the RA coil electrode 25 of FIG. 2 may be positioned in either the superior vena cava or the right atrium.

Another difference relates to the electrode pair 36 of the CS lead 30. Here, instead of electrodes 37 and 38 being distal to the LA coil electrode 35, the electrodes 37 and 38 of the electrode pair 36 are proximal to the LA coil electrode 35.

In all other respects, the systems of FIGS. 1 and 2 are identical.

Both systems provide for the same therapy delivery electrode configurations which will be described subsequently with respect to FIGS. 4–13.

Figure 3:
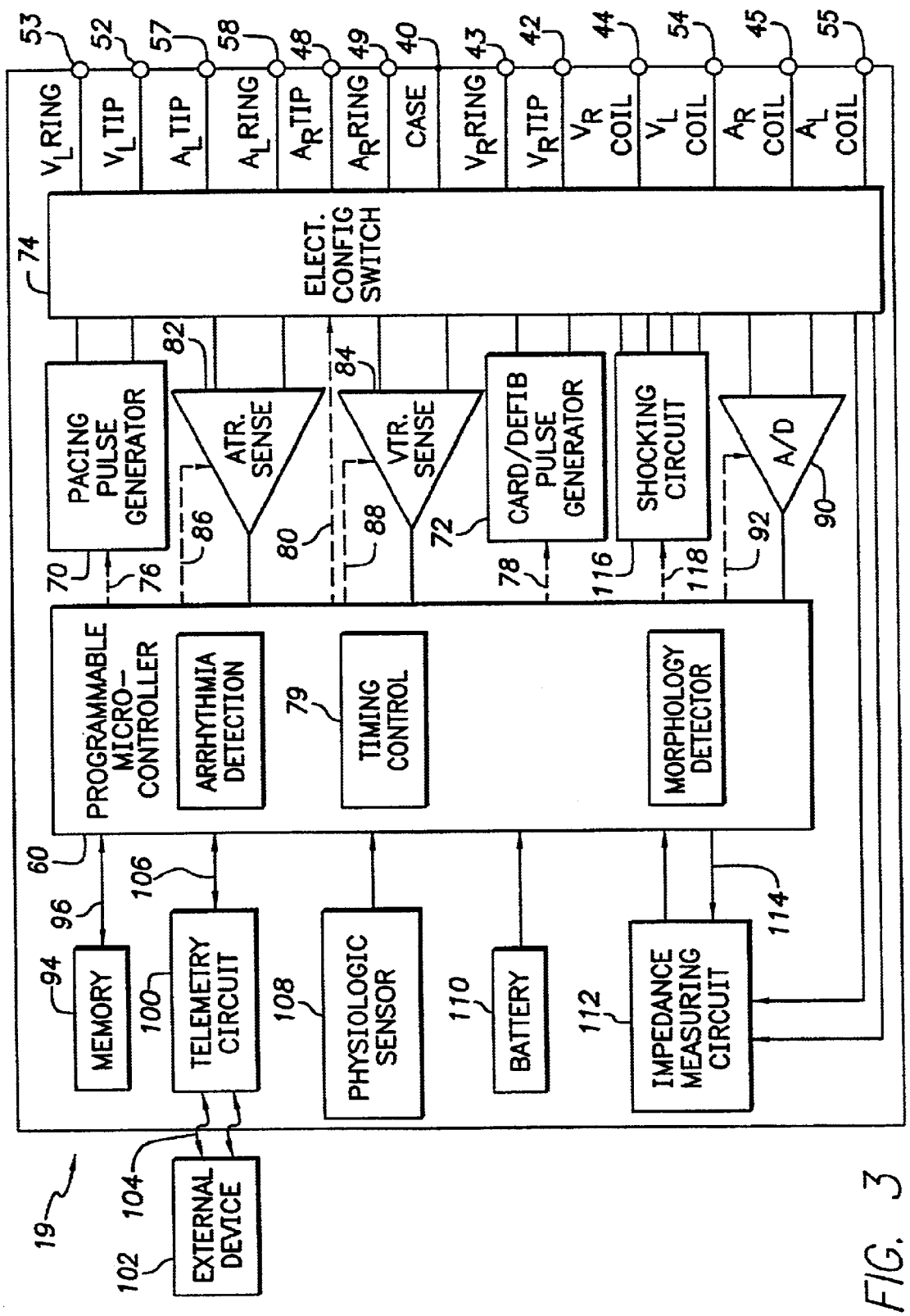
FIG. 3 is a functional block diagram of a multi-chamber implantable stimulation device which may be employed in the systems of FIGS. 1 and 2 and illustrating the basic elements of the stimulation device to provide cardioversion, defibrillation and pacing stimulation in four chambers of the heart.

As illustrated in FIG. 3, a simplified block diagram is shown of the multi-chamber implantable stimulation device 19, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 19, shown schematically in FIG. 3, is often referred to as the "can", "case" or "case electrode" and may be programmably selected to act as an electrode for some of the possible therapy delivery electrode configurations. Hence, the housing 40 may be used in combination with one or more of the coil electrodes, 24, 25, 34 and 35, for defibrillation purposes. The housing 40 further includes a connector (not shown) having a plurality of terminals, 42, 43, 44, 45, 48, 49, 52, 53, 54, 55, 57, and 58 (shown schematically and, for convenience, the names of the electrodes to which they are connected are shown next to the terminals). As such, to achieve right atrial sensing and pacing, the connector includes a right atrial tip terminal ($A_R$ TIP) 48 and a right atrial ring terminal ($A_R$ RING) 49 adapted for connection to the right atrial tip electrode 28 and the right atrial ring electrode 29, respectively.

To achieve left chamber sensing, pacing and shocking, the connector includes a left ventricular tip terminal ($V_L$ TIP) 52, a left ventricular ring terminal ($V_L$ RING) 53, a left atrial ring terminal ($A_L$ RING) 58, a left atrial tip terminal ($A_L$ TIP) 57, a left atrial shocking terminal ($A_L$ COIL) 55, and a left ventricular shocking terminal ($V_L$ COIL) 54 which are adapted for connection to the left ventricular tip electrode 32, the left ventricular ring electrode 33, the left atrial ring electrode 38, the left atrial tip electrode 37, the left atrial coil electrode 35, and the left ventricular coil electrode 34, respectively.

To support right chamber sensing, pacing and shocking, the connector further includes a right ventricular tip terminal ($V_R$ TIP) 42, a right ventricular ring terminal ($V_R$ RING) 43, a right ventricular shocking terminal ($V_R$ COIL) 44, and a right atrial shocking terminal ($A_R$ COIL) 45, which are adapted for connection to the right ventricular tip electrode 22, right ventricular ring electrode 23, the RV coil electrode 24, and the RA coil electrode 25, respectively.

At the core of the stimulation device 19 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 3, an atrial pulse generator 70 and a ventricular pulse generator 72 generate pacing stimulation pulses for delivery by the right atrial lead 26, the right ventricular lead 20, and/or the coronary sinus lead 30 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, secondary defibrillation shock delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 26, coronary sinus lead 30, and the right ventricular lead 20, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 19 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 26, the coronary sinus lead 30, and the right ventricular lead 20 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 19 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 19 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 19 (as contained in the microcontroller 60 or memory 94) to be sent to the external device 102 through an established communication link 104.

In the preferred embodiment, the stimulation device 19 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 3. For the stimulation device 19, which employs shocking therapy, the battery 110 must be capable of operating at low current drains for long periods of time, and then be capable of providing high-current pulses (for capacitor charging) when the patient requires a shock pulse The battery 110 must also have a predictable discharge characteristic so that elective replacement time can be detected. Accordingly, the device 19 preferably employs lithium/silver vanadium oxide batteries, as is true for most (if not all) current devices.

As further shown in FIG. 3, the device 19 is shown as having an impedance measuring circuit 112 which is enabled by the microcontroller 60 via a control signal 114. The impedance measuring circuit 112 is not critical to the present invention and is shown for only completeness.

In the case where the stimulation device 19 is intended to operate as an implantable cardioverter/defibrillator (ICD) device, it must detect the occurrence of an arrhythmia, and automatically apply an appropriate electrical shock therapy to the heart aimed at terminating the detected arrhythmia. As will be seen hereinafter, the shocking therapy may include a single shock to an electrode configuration or a primary shock to one electrode configuration followed, after a secondary shock delay, by a secondary shock to another and different electrode configuration. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through efficacious combinations of the shocking electrodes including the case electrode 40, and as shown in FIGS. 1 and 2, selected from the left atrial coil electrode 35, the RV coil electrode 24, the RA coil electrode 25 and the left ventricular coil electrode 34. As noted above, the housing 40 may also act as an active electrode.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

FIGS. 4–10 show simplified representations of electrode configurations for providing ventricular defibrillation shocks to the heart 11 in accordance with the present invention. The reference numerals identifying the various elements shown in FIGS. 4–10 are identical to those used for corresponding elements shown in FIGS. 1 and 2 for clarity and to illustrate the applicability of the systems of FIGS. 1 and 2 for achieving the electrode configurations shown in each of FIGS. 4–10.

Figure 4:
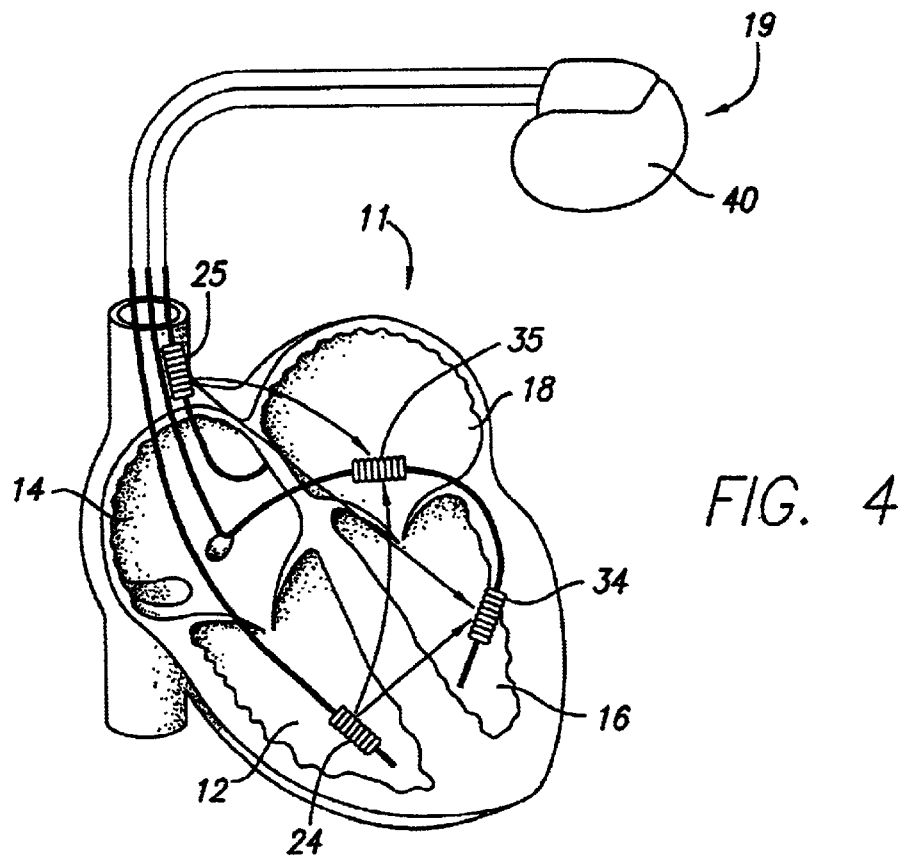
FIG. 4 is a simplified diagram of a first electrode configuration obtainable with the lead systems of FIGS. 1 and 2 for defibrillating the ventricles in accordance with one embodiment of the present invention.

In FIG. 4, two electrode configurations are shown to permit a defibrillation shock to be applied simultaneously to the electrode configurations and between the right heart and the left heart. More specifically, the switch 74 of FIG. 3 may be set to connect the right atrial coil electrode 25 to the right ventricular coil electrode 24 to form a first pole or joint connection and to connect the left atrial coil electrode 35 and the left ventricular coil electrode 34 together to form a second pole or joint connection. After the electrodes are connected in this manner by switch 74, the defibrillation shock is then applied between the first and second poles. This causes the defibrillation shock to be applied simultaneously with the first electrode configuration between the right atrium 14, with the right atrial coil electrode 25, and the left atrium 18 and left ventricle 16, with the left atrial and left ventricular coil electrodes 35 and 34, respectively and with the second electrode configuration between the right ventricle 12, with the right ventricular coil electrode 24, and the left atrium 18 and left ventricle 16, with the left atrial and left ventricular coil electrodes 35 and 34, respectively.

The arrows in FIG. 4 illustrate the direction of defibrillation shock current flow from the base of the arrow (the cathode) to the tip of the arrow (the anode). As is well known in the art, the direction of each of the arrows, and thus the polarity of the shock, may be reversed. In either case, the defibrillation shock is applied across the heart in a right to left direction as illustrated or in a left to right direction if polarity is reversed. This permits a large portion of the ventricular myocardium to be within the shock field for depolarizing the ventricular myocardium.

Figure 5:
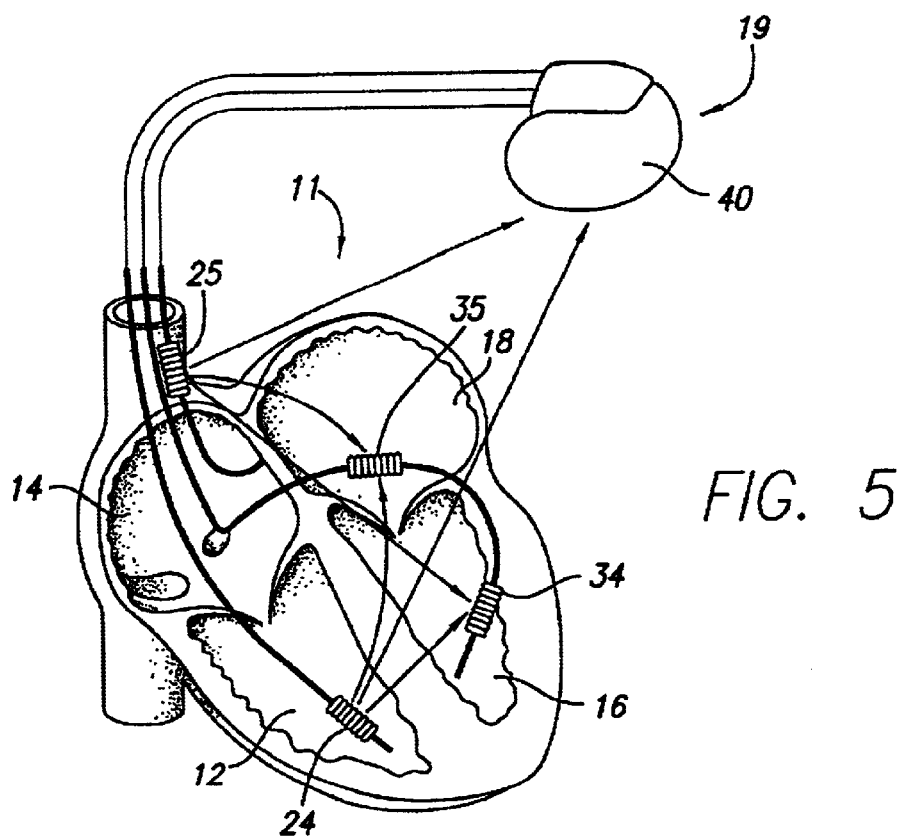
FIG. 5 is a simplified diagram of a second electrode configuration obtainable with the lead systems of FIGS. 1 and 2 for defibrillating the ventricles in accordance with another embodiment of the present invention.

FIG. 5 illustrates a third electrode configuration in addition to the first and second electrode configurations of FIG. 4. Here, the case 40 of the device 19 is used as an electrode. The third electrode configuration is formed by the switch 74 of FIG. 3 connecting the case 40 to the second pole formed by the joint connection of the left ventricular and left atrial coil electrodes 34 and 35. Consistent with the first and second configurations, the third electrode configuration permits the defibrillation shock to be applied between the right heart and the left heart.

Figure 6:
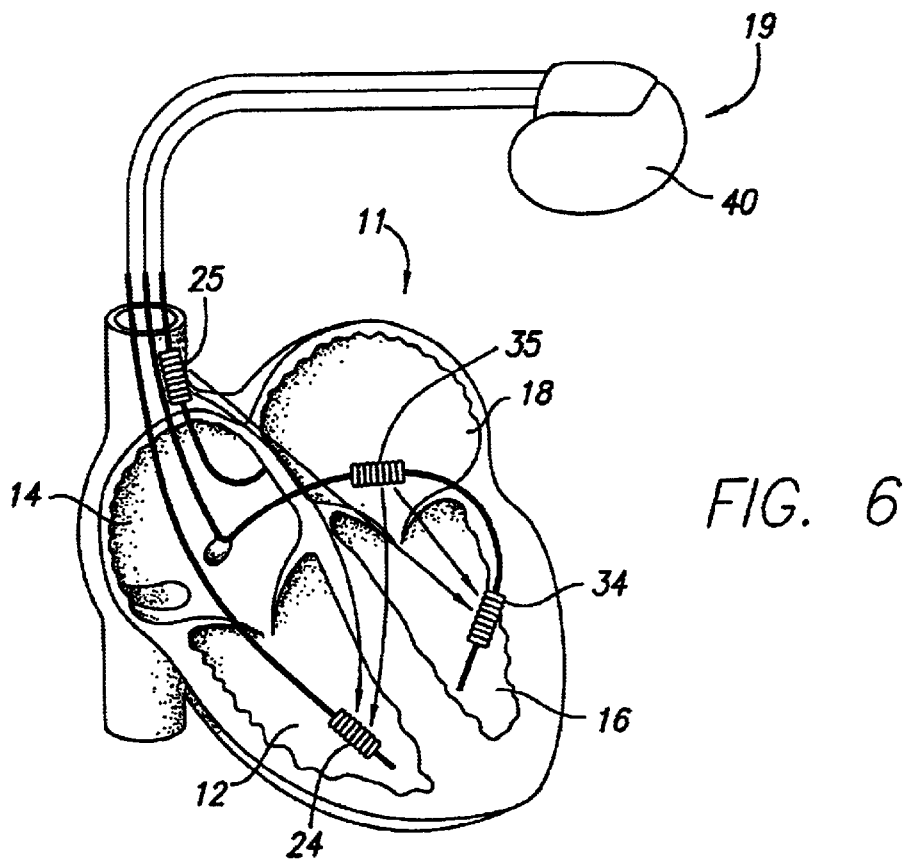
FIG. 6 is a simplified diagram of still another electrode configuration obtainable with the lead systems of FIGS. 1 and 2 for defibrillating the ventricles in accordance with a further embodiment of the present invention.

FIG. 6 also illustrates two electrode configurations across which a defibrillation shock may be simultaneously applied. Here, the defibrillation shock is applied between the apex of the heart and the base of the heart in a bottom to top direction.

More specifically, the switch 74 of FIG. 3 may be set to connect the right atrial coil electrode 25 to the left atrial coil electrode 35 to form a first pole or joint connection and to connect the right ventricular coil electrode 24 and the left ventricular coil electrode 34 together to form a second pole or joint connection. After the electrodes are connected in this manner by switch 74, the defibrillation shock is then applied between the first and second poles. This causes the defibrillation shock to be applied simultaneously with the first electrode configuration between the right atrium 14, with right atrial coil electrode 25, and the right ventricle 12 and left ventricle with the right ventricular and the left ventricular coil electrodes 24 and 34, respectively and with the second electrode configuration between the left atrium 18, with left atrial coil electrode 35, and the right ventricle 12 and left ventricle 16, with the right ventricular and left ventricular coil electrodes 24 and 35, respectively.

As with the previous embodiments, the arrows in FIG. 6 illustrate the direction of defibrillation shock current from the base of the arrow (the cathode) to the tip of the arrow (the anode). As previously described, the directions of each of the arrows, and thus the polarity of the shock, may be reversed. In either case, the defibrillation shock is across the heart in a top to bottom direction as illustrated or in a bottom to top direction if polarity is reversed. This also permits a large portion of the ventricular myocardium to be within the shock field for depolarizing the ventricular myocardium.

Figure 7:
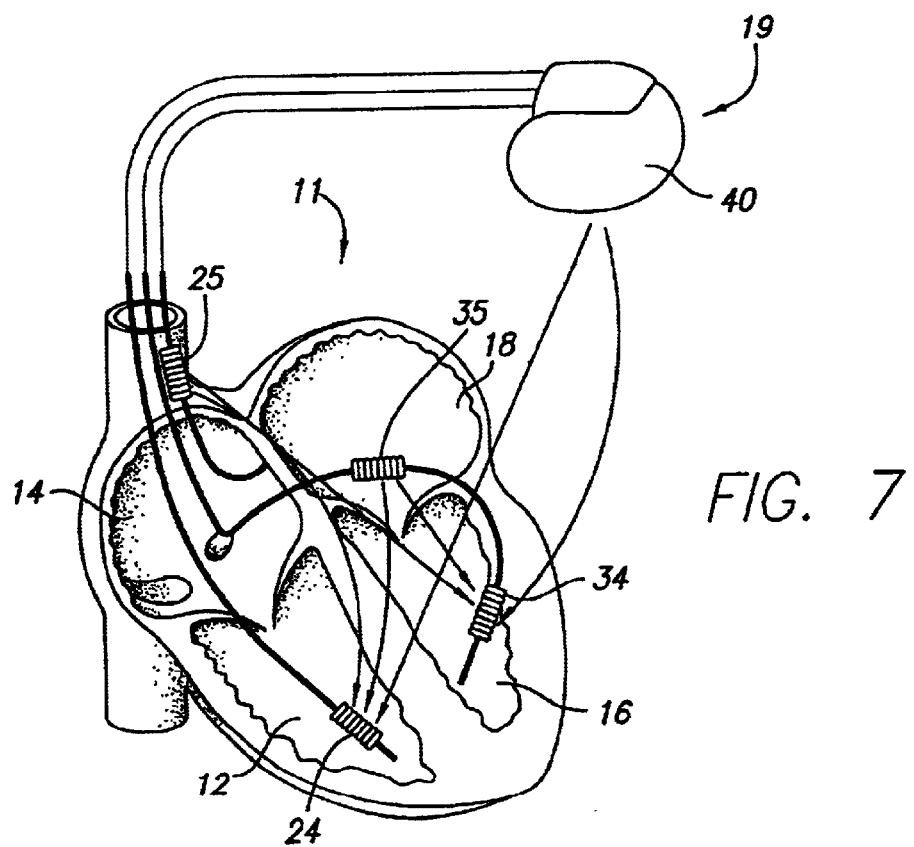
FIG. 7 is a simplified diagram of a further electrode configuration obtainable with the lead systems of FIGS. 1 and 2 for defibrillating the ventricles in accordance with a still further embodiment of the present invention.

FIG. 7 illustrates a third electrode configuration which may be added to the first and second electrode configurations of FIG. 6. Here, the case 40 of device 19 is once again used as an electrode. The third electrode configuration is formed by the switch 74 of FIG. 3 connecting the case 40 to the first pole formed by the joint connection of the right atrial and left atrial coil electrodes 25 and 35, respectively. This permits the defibrillation shock to also be applied between the case 40 of device 19 and the right ventricle 12 and left ventricle 16. Consistent with the first and second electrode configurations, the third electrode configuration permits the defibrillation shock to be applied between the base and apex of the heart in a top to bottom direction.

Figure 8:
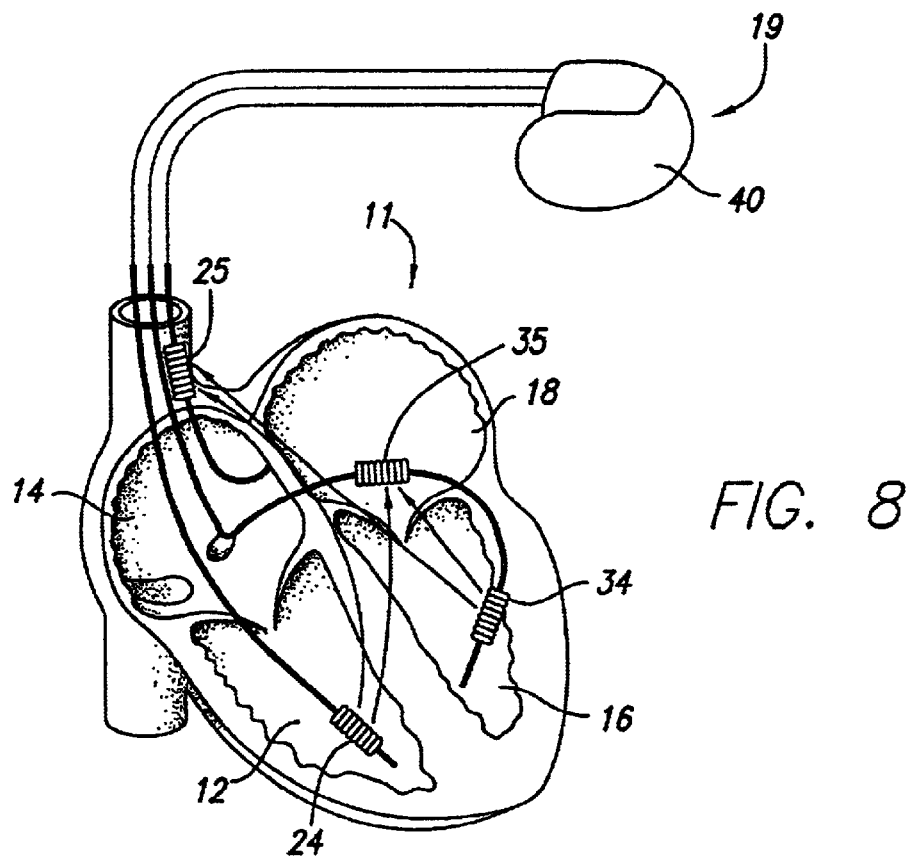
FIG. 8 is a simplified diagram of a still another electrode configuration obtainable with the lead systems of FIGS. 1 and 2 for defibrillating the ventricles in accordance with a still another embodiment of the present invention.

FIG. 8 illustrates the first and second electrode configurations of FIG. 6 with the defibrillation shock pulse polarity reversed. Here, the switch 74 of FIG. 3 is set to connect the right ventricular coil electrode 24 and the left ventricular coil electrode 34 together to form a first pole and the right atrial coil electrode 25 and left atrial coil electrode 35 together to form a second pole. When the defibrillation shock is provided by the device 19, the shock is applied by the first electrode configuration between the right ventricle 12, with the right ventricular coil electrode 24, and the right atrium 14, and left atrium 18, with the right atrial and left atrial coil electrodes 25 and 35, respectively. The shock is simultaneously applied by the second electrode configuration between the left ventricle 16, with the left ventricular coil electrode 34, and the right atrium 14 and left atrium 18, with the right atrial and left atrial coil electrodes 25 and 35, respectively. As a result, the defibrillation shock is applied between the apex and base of the heart in a bottom to top direction. Again, this results in a large portion of the ventricular myocardium to be within the defibrillation field for defibrillating the ventricular myocardium.

Figure 9:
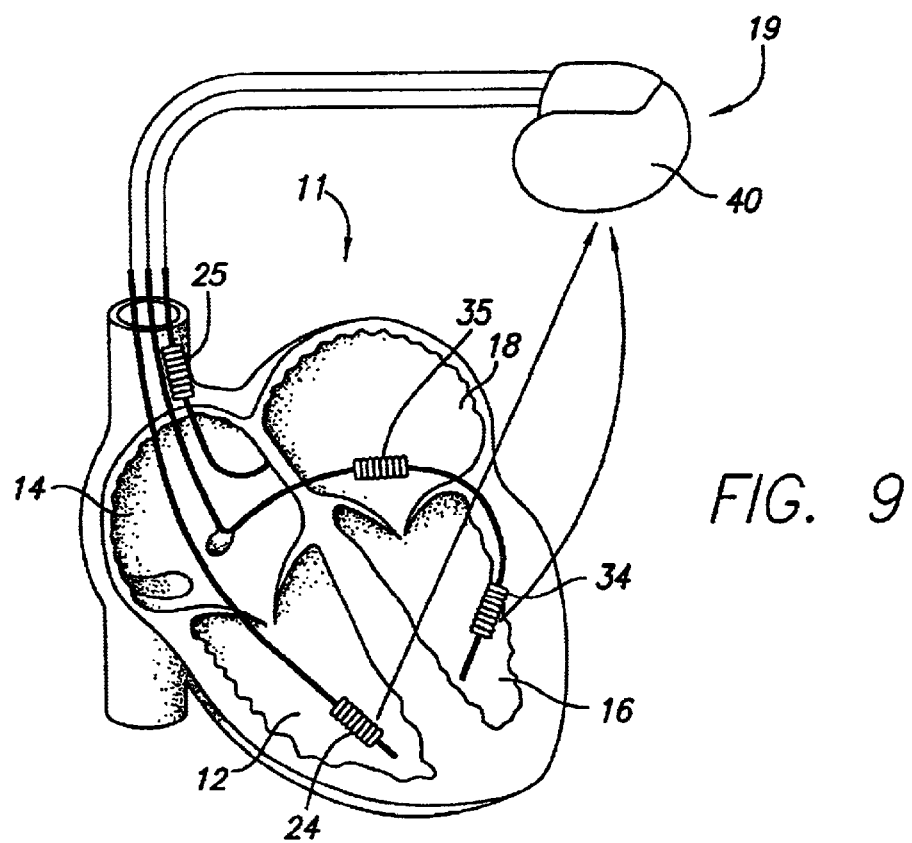
FIG. 9 is a simplified diagram of a further electrode configuration obtainable with the lead systems of FIGS. 1 and 2 for defibrillating the ventricles in accordance with a further embodiment of the present invention.

FIG. 9 illustrates a still further electrode configuration obtainable with the systems of FIGS. 1 and 2 for defibrillating the ventricles 12 and 16 of the heart 11. Here, the heart 11 is defibrillated in a bottom to top direction by making use of the case 40 of the device 19 as an electrode. More specifically, the right ventricular coil electrode 24 and left ventricular coil electrode 34 are connected together by the switch 74 to form a first pole while the case 40 of the device 19 forms the second pole. When the defibrillation shock is provided by the device 19, the defibrillation shock propagates from the right and left ventricles 12 and 16, respectively, to the device case 40. This results in defibrillation of the heart 11 from the apex to the base in a bottom to top direction.

Figure 10:
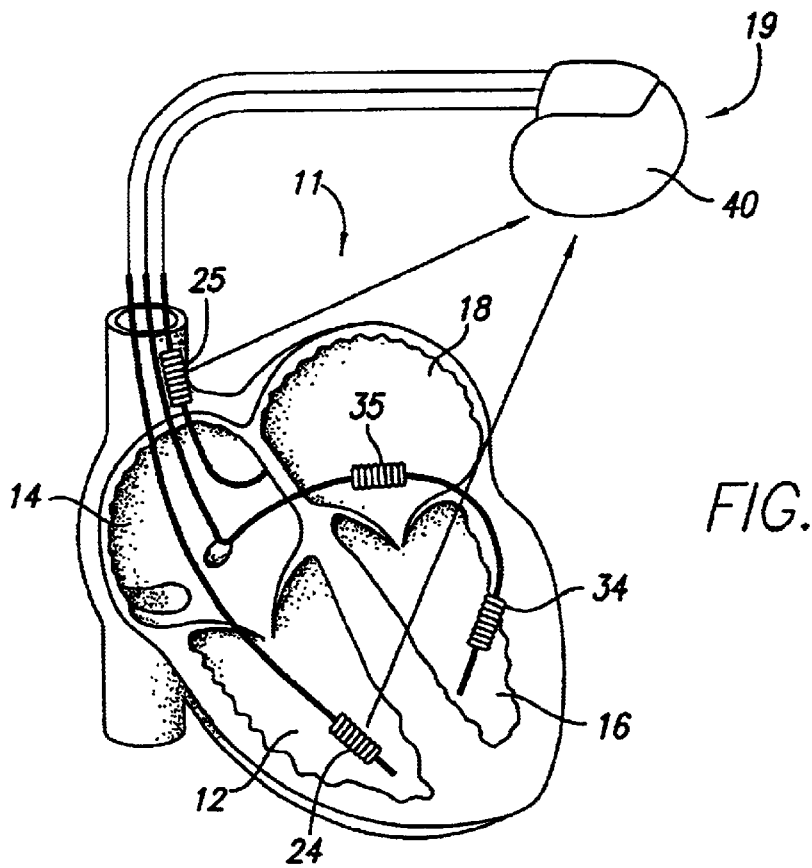
FIG. 10 is a simplified diagram of a further electrode configuration obtainable with the lead systems of FIGS. 1 and 2 for defibrillating the ventricles in accordance with a further embodiment of the present invention.

FIG. 10 illustrates a last example of an electrode configuration obtainable with the system of FIGS. 1 and 2 for defibrillating the ventricles in accordance with the present invention. Here, the heart 11 is defibrillated in a right to left direction by also making use of the case 40 of the device 19 as an electrode. More specifically, the right ventricular coil electrode 24 and the right atrial coil electrode 25 are connected together by the switch 74 of FIG. 3 to form a first pole while the case 40 forms the second pole. When the defibrillation shock is provided by the device 19, the defibrillation shock propagates from the right atrium and right ventricle 14 and 12, respectively, to the device case 40. This results in defibrillation of the heart 11 from the right heart to the left heart for defibrillating the ventricles.

The systems of FIGS. 1 and 2 may also be used to provide sequential defibrillation shocks to the heart for defibrillating the ventricles. As will be appreciated by those skilled in the art, no defibrillation shock alone, applied with implanted electrodes, will depolarize all of the ventricular myocardium. While a large percentage of the ventricular myocardium may be depolarized by utilizing the electrode configurations and methods previously described with reference to FIGS. 4–10, some ventricular myocardium will still not be depolarized. To increase the probability of depolarizing all of the ventricular myocardium, in accordance with the present invention, a secondary defibrillation pulse may be applied using a different electrode configuration, a secondary shock delay after the primary shock. The delay is maintained to be relatively short so that when the secondary shock is delivered, the first portion of the ventricular myocardium depolarized with the primary shock is still depolarized. The secondary shock delay may be, for example, on the order of 10 milliseconds.

Further, in accordance with the present invention, the secondary defibrillation shock is applied with an electrode configuration which results in the secondary shock being applied to the heart substantially orthogonally to the primary defibrillation shock. This may be achieved, for example, by applying the primary shock as illustrated in FIG. 4 (substantially right to left) and then applying the secondary shock as illustrated in FIG. 6 (top to bottom) or FIG. 9 (bottom to top). As a further example, this may be achieved by applying the primary shock as illustrated in FIG. 6 (top to bottom) and then applying the secondary shock as illustrated in FIG. 10 (right to left). As a still further example, the primary shock may be applied as illustrated in FIG. 5 (right to left) and then the secondary pulse applied as illustrated in FIG. 8 (bottom to top). As a last example, the primary shock may be applied as illustrated in FIG. 7 (top to bottom) and then the secondary shock may be applied as illustrated in FIG. 5 (right to left).

In each of the above examples, the first and second defibrillation shocks are applied substantially orthogonally to each other with the secondary shock occurring while the first portion of the heart, depolarized by the primary shock, is still depolarized. In this manner, the secondary shock is available to depolarize what ventricular myocardium remains to be depolarized following the primary shock. Because the shocks are delivered substantially orthogonally to each other, the probability of the secondary shock capturing any ventricular myocardium remaining to be depolarized is substantially enhanced.

Figure 11:
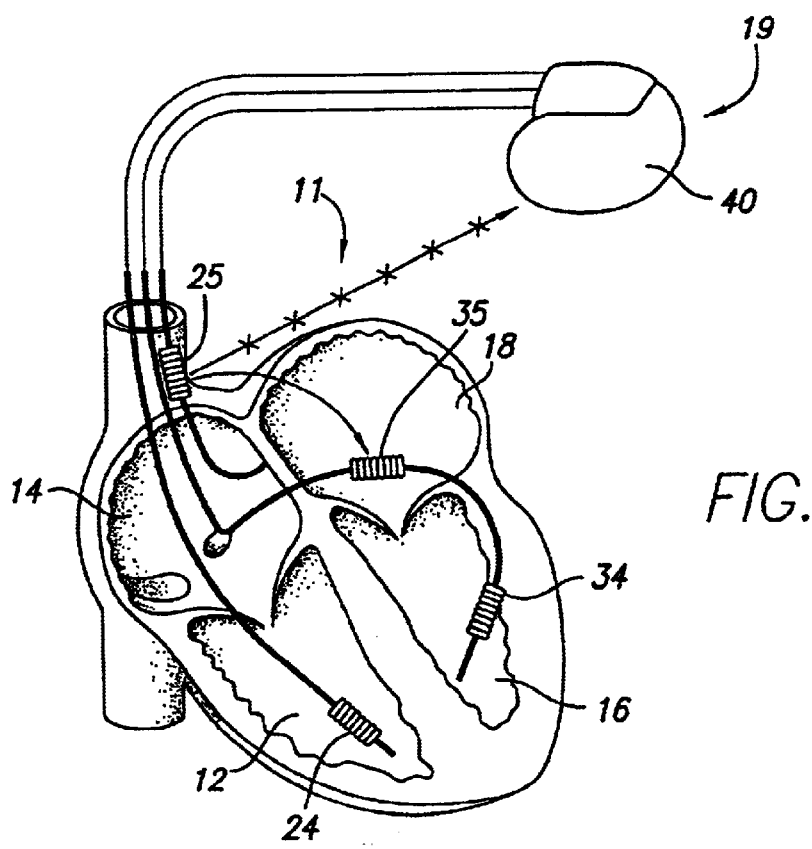
FIG. 11 is a simplified diagram of electrode configurations obtainable with the lead systems of FIGS. 1 and 2 for defibrillating the atria in accordance with the present invention.
Figure 12:
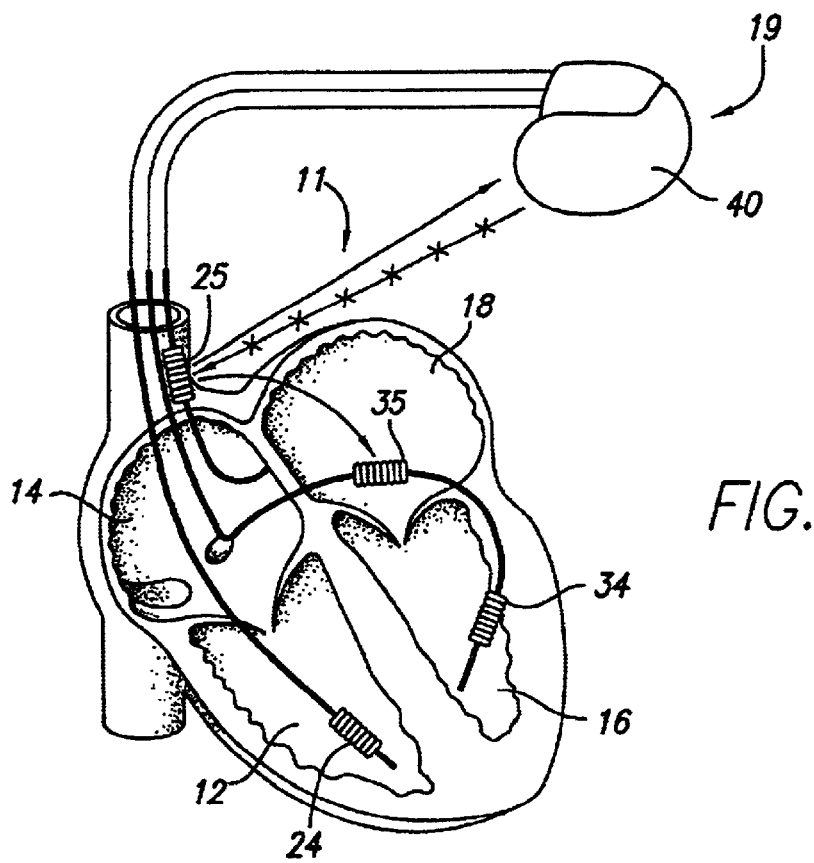
FIG. 12 is a simplified diagram of further electrode configurations obtainable with the lead systems of FIGS. 1 and 2 for defibrillating the atria in accordance with another embodiment of the present invention.
Figure 13:
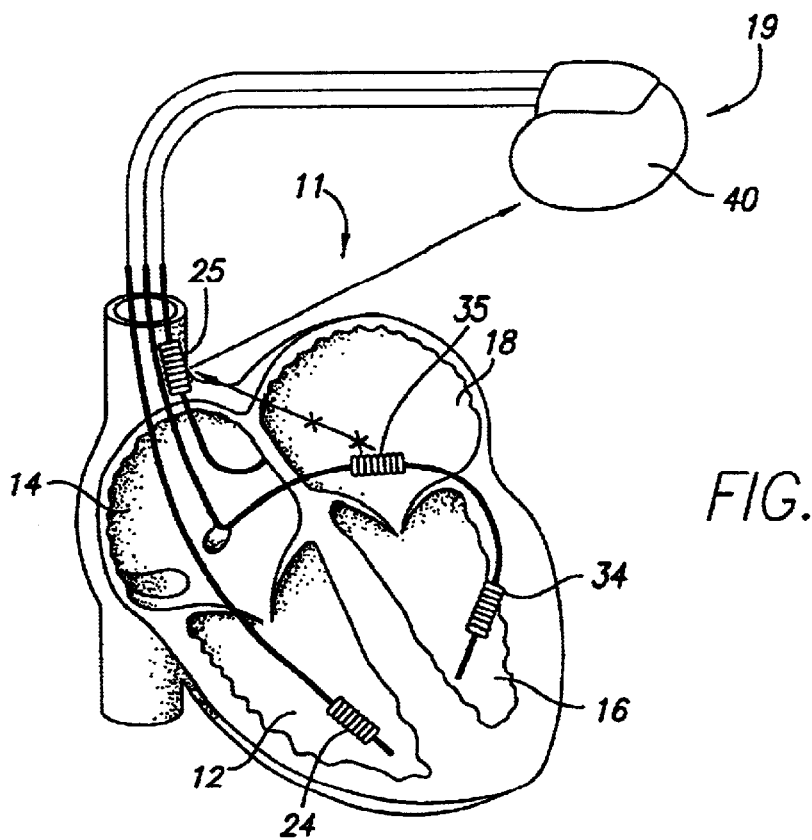
FIG. 13 is a simplified diagram of the still further electrode configurations obtainable with the lead systems of FIGS. 1 and 2 for defibrillating the atria in accordance with a still another embodiment of the present invention.

Similarly, in accordance with further aspects of the present invention, sequential shocks may also be employed for defibrillating the atria. FIGS. 11–13 illustrate examples.

As shown in FIG. 11, a first shock may be applied between the right atrium 14 and left atrium 18 using the right atrial coil electrode 25 and the left atrial coil electrode 35. While the atrial myocardium depolarized by the primary shock is still depolarized, a secondary atrial defibrillation shock is applied between the right atrium 14, with right atrium coil electrode 25, and the case 40 of device 19.

In FIG. 12 a first atrial defibrillation shock is applied between the right atrium 14, using right atrial coil electrode 25, and the combination of the case 40 of device 19 and the left atrium 18, using the left atrial coil electrode 35. The primary shock is then followed by a secondary shock applied between the right atrium 14, using right atrial coil electrode 25, and the case 40 of device 19.

Lastly, FIG. 13 illustrates an example similar to FIG. 11. Here, the primary shock is applied between the right atrium 14, using right atrial coil electrode 25, and the case 40 of device 19. The secondary shock then follows between the left atrium 18, using left atrial coil electrode 35 and the right atrium 14, using right atrial coil electrode 25.

The electrode configurations and methods illustrated in FIGS. 11–13 provide efficacious defibrillation of the atria. The secondary shocks are available to depolarize remaining atrial myocardium not depolarized by the primary shocks. The probability of complete depolarization is enhanced because the primary and secondary shocks are applied in different directions.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A method of stimulating a heart with an implantable cardiac stimulation system, the method including the steps of:

applying a stimulation pulse with a first electrode configuration between a first chamber of the heart and third and fourth chambers of the heart; and simultaneously applying the stimulation pulse with a second electrode configuration between a second chamber of the heart and the third and fourth chambers of the heart, one of the chambers of the heart being the left ventricle.

2. The method of claim 1 wherein the first chamber is the right atrium, the second chamber is the right ventricle, the third chamber is the left atrium and the fourth chamber is the left ventricle.

3. The method of claim 1 wherein the implantable cardiac stimulation system includes a stimulation device having a conductive case and wherein the method further includes the step of simultaneously applying the stimulation pulse with a third electrode configuration between the first and second chambers and the case.

4. The method of claim 3 wherein the first chamber is the right atrium, the second chamber is the right ventricle, the third chamber is the left atrium and the fourth chamber is the left ventricle.

5. A method of stimulating the ventricles of a heart with an implantable cardiac stimulation system, the method including the steps of:

placing a right atrial defibrillation electrode in electrical contact with the right atrium of the heart, a right ventricular defibrillation electrode in electrical contact with the right ventricle of the heart, a left atrial defibrillation electrode in electrical contact with the left atrium of the heart and a left ventricular defibrillation electrode in electrical contact with the left ventricle of the heart;

forming a first common connection of a first plurality of the defibrillation electrodes;

forming a second common connection of a second plurality of the defibrillation electrodes including the left ventricular defibrillation electrode; and delivering a stimulation pulse between the first and second common connections.

6. The method of claim 5 wherein the first plurality of the defibrillation electrodes is the right atrial defibrillation electrode and the left atrial defibrillation electrode and the second plurality of the defibrillation electrodes further includes the right ventricular defibrillation electrode.

7. The method of claim 6 wherein the stimulation system includes a stimulation device including a conductive case and wherein the first plurality of the defibrillation electrodes further includes the conductive case.

8. The method of claim 5 wherein the step of placing a left ventricular defibrillation electrode in electrical contact with the left ventricle of the heart includes placing the left ventricular defibrillation electrode within the coronary sinus region of the heart adjacent the left ventricle.

9. The method of claim 5 wherein the step of placing a left atrial defibrillation electrode in electrical contact with the left atrium of the heart includes placing the left atrial defibrillation electrode with the coronary sinus of the heart adjacent the left atrium.

* * * * *